(12) United States Patent
Kaschak (10) Patent No.: US 7,393,442 B2
(45) Date of Patent: Jul. 1, 2008

(54) EX-SITU PEM FUEL CELL TESTING: TOWARDS VISUALIZING GAS DIFFUSION

(75) Inventor: David M. Kaschak, Olmsted Falls, OH (US)

(73) Assignee: GrafTech International Holdings Inc., Parma, OH (US)

( * ) Notice: Subject to any disclaimer, the term of this patent is extended or adjusted under 35 U.S.C. 154(b) by 777 days.

(21) Appl. No.: 10/925,676

(22) Filed: Aug. 25, 2004

(65) Prior Publication Data
US 2005/0034988 A1      Feb. 17, 2005

Related U.S. Application Data

(63) Continuation of application No. 10/224,853, filed on Aug. 21, 2002, now Pat. No. 6,841,387.

(51) Int. Cl.
*G01N 21/63*        (2006.01)
(52) U.S. Cl. ............... 204/431; 204/433; 204/435; 204/630; 324/438; 422/55; 422/82.07; 422/82.08
(58) Field of Classification Search ............ 204/431, 204/432, 433, 435, 630; 205/437, 787.5, 205/789, 793.5; 210/96.1, 743; 324/438; 422/82.07, 82.08, 55; 436/6, 172; 429/27, 429/29, 30
See application file for complete search history.

(56) References Cited

U.S. PATENT DOCUMENTS

| | | | |
|---|---|---|---|
| 2,273,795 A | * | 2/1942 | Heise et al. ............ 205/437 |
| 3,350,636 A | * | 10/1967 | Winsel ................ 205/787.5 |
| 4,495,002 A | | 1/1985 | Anello .................. 148/12 |
| 4,495,052 A | | 1/1985 | Brezinski ............ 204/435 |
| 4,988,583 A | | 1/1991 | Watkins et al. .......... 429/30 |
| 5,268,092 A | | 12/1993 | Eden .................. 210/96.1 |
| 5,300,370 A | | 4/1994 | Washington et al. ...... 429/34 |
| 5,411,889 A | * | 5/1995 | Hoots et al. ............ 436/6 |
| 6,913,849 B2 | | 7/2005 | Mallouk et al. .......... 429/30 |

FOREIGN PATENT DOCUMENTS

WO          9516287        6/1995

OTHER PUBLICATIONS

Reddington, et. al. Combinatorial Electrochemistry: A Highly Parallel, Optical Screening Method for Discovery of Better Electrocatalysts, Science, 280, 1735-1737 (1998).

Tillmetz, W., Ph.D. Thesis, Technical Institute of Munich (Anorganisch-Chemisches Institut der Technischen Univeritat Munchen), 1984, p. 228-230.

* cited by examiner

*Primary Examiner*—Joseph W Drodge
(74) *Attorney, Agent, or Firm*—Waddey&Patterson, PC; James R. Cartiglia (57) ABSTRACT

The invention comprises novel apparatuses and testing methods for evaluating a fluid diffusion component. The apparatus includes a fluid capable of undergoing oxidation or reduction, a half-cell electrode assembly able to receive the fluid, and a change in acidity indicator in communication with the assembly. An inventive method of the invention includes the steps of passing a fluid capable of undergoing oxidation or reduction through a half-cell electrode assembly to form a sample, contacting the sample with an indicator, and detecting a change in acidity in the indicator.

7 Claims, 3 Drawing Sheets

EX-SITU PEM FUEL CELL TESTING: TOWARDS VISUALIZING GAS DIFFUSION

This application is a Continuation of application Ser. No. 10/224,853, filed on Aug. 21, 2002, now Pat. No. 6,841,387.

FIELD OF THE INVENTION

The invention relates generally to fuel cells and particularly to methods and apparatuses for evaluating individual components of a fuel cell and assemblies of two or more components of the fuel cell.

TECHNICAL BACKGROUND

An ion exchange membrane fuel cell, more specifically a proton exchange membrane (PEM) fuel cell, produces electricity through the chemical reaction of hydrogen and oxygen in the air. Within the fuel cell, electrodes, denoted as anode and cathode, surround a polymer electrolyte to form what is generally referred to as a membrane electrode assembly, or MEA. Oftentimes, the electrodes also function as the gas diffusion layer ("GDL") of the fuel cell. A catalyst material stimulates hydrogen molecules to split into hydrogen atoms and then, at the membrane, the atoms each split into a proton and an electron. The electrons are utilized as electrical energy. The protons migrate through the electrolyte and combine with oxygen and electrons to form water.

A PEM fuel cell includes a membrane electrode assembly sandwiched between two graphite flow field plates. Conventionally, the membrane electrode assembly consists of random-oriented carbon fiber paper electrodes (anode and cathode) with a thin layer of a catalyst material, particularly platinum or a platinum group metal coated on isotropic carbon particles, such as lamp black, bonded to either side of a proton exchange membrane disposed between the electrodes. In operation, hydrogen flows through channels in one of the flow field plates to the anode, where the catalyst promotes its separation into hydrogen atoms and thereafter into protons that pass through the membrane and electrons that flow through an external load. Air flows through the channels in the other flow field plate to the cathode, where the oxygen in the air is separated into oxygen atoms, which joins with the protons through the proton exchange membrane and the electrons through the circuit, and combine to form water. Since the membrane is an insulator, the electrons travel through an external circuit in which the electricity is utilized, and join with protons at the cathode. An air stream on the cathode side is one mechanism by which the water formed by combination of the hydrogen and oxygen is removed. Combinations of such fuel cells are used in a fuel cell stack to provide the desired voltage.

The flow field plates have a continuous reactant flow channel with an inlet and an outlet. The inlet is connected to a source of fuel in the case of an anode flow field plate, or a source of oxidant in the case of a cathode flow field plate. When assembled in a fuel cell stack, each flow field plate functions as a current collector.

Electrodes, also sometimes referred to as gas diffusion layers, may be formed by providing a graphite sheet as described herein and providing the sheet with channels, which are preferably smooth-sided, and which pass between the parallel, opposed surfaces of the flexible graphite sheet and are separated by walls of compressed expandable graphite. It is the walls of the flexible graphite sheet that actually abut the ion exchange membrane, when the inventive flexible graphite sheet functions as an electrode in an electrochemical fuel cell.

The channels are formed in the flexible graphite sheet at a plurality of locations by mechanical impact. Thus, a pattern of channels is formed in the flexible graphite sheet. That pattern can be devised in order to control, optimize or maximize fluid flow through the channels, as desired. For instance, the pattern formed in the flexible graphite sheet can comprise selective placement of the channels, as described, or it can comprise variations in channel density or channel shape in order to, for instance, equalize fluid pressure along the surface of the electrode when in use, as well as for other purposes which would be apparent to the skilled artisan.

The aforementioned PEM fuel cells are being developed as an alternative energy source for portable, stationary, and industrial applications. Significant R&D efforts in the fuel cell area are being directed towards the science of fuel cell technology as well as in the areas of engineering and systems integration. A common need at the heart of all PEM systems is to increase the understanding of molecular level interactions within the system including gas flow to the membrane electrode assembly ("MEA"), diffusion, kinetics, thermodynamics of reactants and products of the electrochemical reaction, water management, heat transfer, and current collection.

Presently, diagnostic systems like fuel cell test stations are available which allow performance testing of stack-level component integration, combined with electronic measurements for performance evaluations, these systems are very costly, complex, and time consuming to operate. Additionally, individual component characterization and material evaluation is potentially possible through the use of classic electrochemical, and materials characterization methodologies such as X-ray diffraction, Potentiostatic/Galvanostatic measurements, impedance analysis, and microscopy.

As an example of industry shortcomings in the testing regime, Gurley porosity is commonly utilized to give an indication of the permeability of a fuel gas (e.g., hydrogen) through gas diffusion layer substrates. While Gurley porosity is useful for initial material screening purposes, direct correlation to operational performance is difficult. Also Gurley porosity does not include any specificity towards a correlation with the electrochemical reaction that takes place at the anode or cathode. Furthermore, localized differences in gas diffusion rates are difficult to detect.

There is a lack of availability, of intermediate testing paradigms that elucidate material and component integration, below the stack-level or even single cell level integration (ex-situ). Also there is need for testing methods to evaluate component performance functions under conditions that simulate real fuel cell operation. Furthermore, there is a need for a quick cost-effective testing paradigm for components.

SUMMARY OF THE INVENTION

One aspect of the invention is a fluid diffusion testing apparatus. The apparatus includes a fluid capable of undergoing oxidation or reduction. The apparatus further includes a half-cell electrode assembly capable to receive the fluid. Additionally, the apparatus includes a change in acidity indicator in communication with the assembly.

Another aspect of the invention is a method of testing a fluid diffusion assembly. The method includes the step of passing a fluid capable of undergoing oxidation or reduction through a half-cell electrode assembly to form a sample. The sample contacts an indicator. A change in acidity of the indicator is detected.

A further aspect of the invention is a method for selecting a fluid permeable element for a proton exchange membrane fuel cell. The method includes the steps of (a) passing a fluid capable of undergoing oxidation or reduction through a half-cell electrode assembly to form a sample;

(b) contacting the sample with an indicator; (c) observing at least one concentration gradient of the sample in the indicator; (e) conducting the above steps (a)-(d) on a plurality of half-cell electrode assemblies; and (f) selecting the half-cell electrode from the plurality with the most uniform concentration of the sample in the indicator.

An additional aspect of the invention is a method of visualizing gas diffusion. The method of visualizing gas diffusion includes the step of passing a fluid capable of undergoing oxidation or reduction through a half-cell electrode assembly to form a sample. The method further includes the step of the sample contacting an indicator. Another step of the method is observing at least one concentration gradient of the sample in the indicator.

Furthermore, aspects of the invention include a method of measuring gas diffusion. The method of measuring gas diffusion also includes the steps of passing a fluid capable of undergoing oxidation or reduction through a half-cell electrode assembly to form a sample and contacting the sample with an indicator. The method of measuring gas diffusion further includes the step of determining a difference in the pH of a mixture of the indicator and the sample as compared to the pH of the indicator substantially free of the sample.

One advantage of the invention includes the ability to visualize the gas diffusion activity in PEM half-cell reactions. In an embodiment of the invention, this is accomplished via a novel integration of fluorescent pH detection or a colorimetric dye with materials that may be used in a PEM fuel cell.

Another advantage of the invention is that the invention can be used to focus on parameters related to spatial visualization of gas diffusion, catalyst uniformity verification, and fuel delivery through gas diffusion layer(s) to the catalyst.

A further advantage of the invention is that it may be practiced to test various components of a fuel cell, individually or in combination with each other, at conditions that truly resemble the operating conditions of the cell.

Furthermore, the advantages include that the invention may be used to evaluate differences in gas diffusion properties between materials whose function is to diffuse a fluid. This may be accomplished by visualization of active surface sites and the spatial resolution of the sites for the material, which represents the anodic dissociation of hydrogen (in one case) in the separation of protons and electrons (or the consumption of protons in the case of the cathode reaction).

Additionally, the invention will accelerate the state of the art understanding of component functions within an operating fuel cell, and provide a tool to assist in rapidly commercializing the fuel cell through optimized component integration. The invention also provides testing paradigms for sub-stack and sub-cell material assembly and component integration. Furthermore, the inventive apparatus can be used to obtain ex-situ diagnostic outputs with respect to component functionality.

Additional features and advantages of the invention will be set forth in the detailed description which follows, the claims, as well as the appended drawings.

It is to be understood that both the foregoing general description and the following detailed description present embodiments of the invention, and are intended to provide an overview or framework for understanding the nature and character of the invention as it is claimed. The accompanying drawings are included to provide a further understanding of the invention, and are incorporated into and constitute a part of this specification. The drawings illustrate various embodiments of the invention, and together with the description serve to explain the principles and operations of the invention.

DETAILED DESCRIPTION OF THE INVENTION

Figure 1:
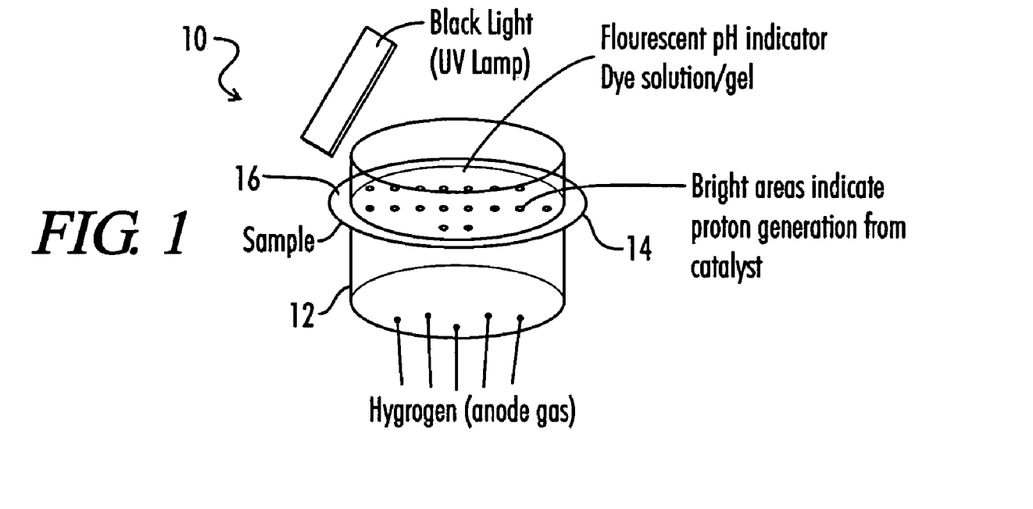
FIG. 1 is a side schematic representation of a fluid diffusion testing apparatus.

The invention will be further described in regards to the accompanying drawings. Whenever possible, like or the same reference numerals may be used to describe like or the same elements. Illustrated in FIG. 1 is a schematic representation of a fluid diffusion testing apparatus, generally designated 10. The embodiment of the apparatus 10 illustrated in FIG. 1 is an electrochemical cell allowing the anode half-cell reaction of preferably, but not limited to, $H_2 2H^+ + 2e^-$. In the same manner the half-cell reaction of other proton generating fuels can be utilized for any PEM reaction, such as methanol (MeOH). The aforementioned reaction may also be known as the anode reaction or an oxidation reaction. The invention is not limited to the aforementioned reaction. The invention is equally applicable to a cathode half-cell reaction, such as, but not limited to, $2H^+ + O^{-2} H_2O$. The cathode half-cell reaction may also be known as a reduction reaction or cathode reaction.

Apparatus 10 includes a fluid capable of undergoing oxidation or reduction. One example of a fluid able to undergo an oxidation reaction comprises hydrogen. An example of a fluid capable of undergoing reduction comprises a proton such as $H^+$. Preferably, the hydrogen gas was generated from an electrolyzer, not shown in FIG. 1. Other sources of the fluid may also be used. For example, if the fluid comprises oxygen, potential sources include air and bottled oxygen. Additionally, humidity could be a potential source for oxygen or hydrogen. Fluid is used herein to mean a composition of matter that is either in the gas phase, liquid phase, or some combination of both. As shown in FIG. 1, the fluid may be passed through a tube 12. Preferably tube 12 includes a flange 14.

A half-cell electrode assembly 16 capable to receive the fluid is aligned to receive the fluid in fluid 14. Preferably assembly 16 is able to generate a proton or able to reduce a proton, as described above. Furthermore, the aforementioned half-cell oxidation or reduction reaction takes place at assembly 16. Preferably, assembly 16 includes a catalyst for one of the aforementioned oxidation or reduction reactions. The catalyst may also comprise an ink.

Examples of suitable catalysts comprise transition metals, preferably noble metals, such as platinum, gold, silver, palladium, ruthenium, rhodium, osmium, and iridium, and combinations thereof. A preferred catalyst is platinum black on carbon, or platinum/ruthenium on carbon.

Optionally, assembly 16 may also include a fluid permeable element. The fluid permeable element may be an integral part of assembly 16 or, alternatively, adjacent the catalyst. It is preferred that the fluid permeable member and the catalyst are in communication, meaning that the fluid can be passed from the fluid permeable member to the catalyst. Preferably, the fluid permeable element comprises at least one of a gas diffusion layer, a gas diffusion substrate, flow field plate, and combinations thereof. Preferably, the gas diffusion substrate comprises at least one of a sheet of flexible graphite, a carbon fiber paper, a composite of flexible graphite and a polymer, a composite of carbon and a polymer, and a composite of flexible graphite, carbon, and a polymer. Other suitable diffusion substrates comprise cotton fiber, glass fiber, polymer asbestos, cardboard, aluminum oxide membrane, zeolite substrate, and inorganic fiber (e.g., mullite). Examples of suitable polymers include phenolic resins, acrylic resins, and epoxy resins. Optionally, the polymer may be in the form of a fiber or a perforated sheet. One example of flexible graphite is GRAF-CELL™, from Graftech Inc. of Lakewood, Ohio. Optionally, the sheet of flexible graphite may have at least one perforation, preferably a plurality of perforations. Preferably, the perforation is aligned in communication with the catalyst. Optionally, the gas diffusion layer may comprise a carbon coating, a carbon black coating, a polytetrafluoroethylene coating or mixtures thereof.

In addition to the catalyst and the optional fluid permeable element, apparatus 10 may also include a membrane (also referred to as an electrolyte). Preferably, the membrane comprises a solid polymer electrolyte (also referred to as a solid polymer ion exchange membrane) that is an electrically insulating material. More preferred the insulating material is substantially gas-impermeable and substantially ion-permeable. Suitable solid polymer materials include films of perfluorinated sulfonic acids derived from fluorinated styrenes, quaternary amine polystyrene, polybenzimidazole ("PBI"), or other ionomeric polymers.

As for properties, it is preferred that the membrane has excellent mechanical strength, predictable dimensional changes, high electrical conductivity, and the ability to transport the desired ions while rejecting the undesired ions and molecules.

With respect to the membrane, examples of suitable membrane materials include, but are not necessarily limited to, NAFION® products available from Dupont of Wilmington, Del., the Dow membrane materials available from Dow Chemical Co., of Midland, Mich., the Gore-Select™ materials available from W.L. Gore & Associates, Inc, of Wilmington, Del. In an alternate embodiment of assembly 16, the membrane may be an integral part of the catalyst or separate and apart from the catalyst.

For additional background regarding the catalyst, the fluid permeable element, the membrane, or other basic elements of an electrochemical fuel cell, the specifications of U.S. Pat. Nos. 4,988,583 and 5,300,370 and PCT WO 95/16287 are incorporated herein by reference in their entirety.

Optionally, in the case of the oxidation reaction, it is preferred that assembly 16 performs the function of removing the electron ($e^-$) from apparatus 10. One technique to remove the electron from apparatus 10 is to ground apparatus 10.

Preferably, apparatus 10 also includes a change in acidity indicator 18. It is preferred that indicator 18 is in communication with assembly 16. Communication is used herein to mean that matter may flow into assembly 16 and at least the desired material (e.g., proton, electron, or reduced specie) may pass into indicator 18, or that indicator 18 may detect the generation of the desired material by some other means. Preferably, indicator 18 receives the desired material from assembly 16. The desired material may also be referred to as the product of the reaction or the "sample." The sample is used herein to describe the proton generated or the compound reduced depending on whether the half-cell reaction is a cathode reaction or an anode reaction. Indicator 18 does not require an aqueous medium or any other sort of aqueous environment.

In one embodiment, indicator 18 comprises a fluorescent pH indicator and an UV lamp aligned to illuminate the fluorescent pH indicator. Optionally, the fluorescent pH indicator may comprise a solution in the form of a liquid or a gel. Preferably, the gel may comprise a hydrophilic material, more preferably a hydrophilic material that swells in the presence of water. Preferred types of the fluorescent pH indicators include any element or matter that is able to detect a pKa range of acidity that is generated by the half-cell reaction such as a pH sensitive dye. Sources of pH sensitive dyes include Aldrich of St. Louis, Mo. or Molecular Probes Inc. of Eugene, Oreg. One such pH sensitive dye comprises quinine. Examples of other types of fluorescent pH indicators include Eosin B, Eosin Y, and Fluorescein. Eosin B and Eosin Y both comprise disodium salts. A preferred type of UV lamp is a black lamp and a preferred range of wavelengths comprises at least about 250 nm and no more than about 400 nm. One source of a suitable UV lamp is Fisher Scientific of Springfield, N.J.

Another example of a suitable indicator 18 would be a colorimetric dye. Preferably, the calorimetric dye will change color upon transfer of the sample (proton, electron, or a reduced specie) to indicator 18. For example, upon the aforementioned transfer of the sample, the calorimetric dye may change colors from clear to a particular color (e.g., red or green) or vice versa. In another embodiment, the colorimetric dye may change from one color to another such as from red to green upon the transfer. Phloxine B from Aldrich Chemical Co. is one example of a suitable calorimetric dye. In a generic sense, Phloxine B comprises spiro[isobenzofuran-1(3H),9'-[9H]xanthen-3-one, 2'4'5'7'-tetrabromo-4,5,6,7-tetrachlor-3'6'-dihydroxy-,disodium salt.

Preferably, the colorimetric dye does not require the presence of a UV lamp to observe the aforementioned color change. Preferably, the lighting available is ambient or room light available from any type of common household light bulb or sunlight. Therefore, an advantage to using a colorimetric dye as an indicator is that a UV lamp would not be needed.

In a third embodiment, indicator 18 may comprise a potentiometric dye to measure a current generated during the reaction that takes place at the catalyst, with or without a calorimetric dye or a fluorescent pH indicator. Also various types of hardware that may be used to detect a change in indicator 18 include a fluorescent microscope with or without a band pass filter, or an imaging microscope wavelength light detector such as a Near-field Scanning Optical Microscopy (NSOM). An advantage of the hardware is that the hardware is able to detect a change in indicator 18 with higher resolution than that of the human eye.

In specific embodiments, indicator 18 may comprise a solution of a pH indicator and a host. Examples of suitable hosts includes water, Nafion® (a perfluorinated sulfonic acid), an organic solvent, or a catalyst support. The host may act as a binder to adhere indicator 18 to assembly 16. The host may maintain indicator 18 in contact with the catalyst. Optionally, the solution may include at least one stabilizer, at least one viscosity enhancer and/or at least one component able to transfer current. The viscosity enhancer may be used to control the viscosity of indicator 18 such that indicator 18 have a viscosity associated with a gel or a liquid. An example of a suitable stabilizer is ethylenediamne tetraacetic acid ("EDTA"). Other examples of suitable viscosity enhancers include glycerin, gel, oil, guar gum, methyl cellulose, and hydrous magnesium clay, e.g., Laponite®. Examples of components able to transfer current include NaCl, $NaClO_4$, $NaPF_6$, $NaBF_4$, and mixtures thereof.

In practice, it is possible to apply a two or three terminal electrochemical diagnostic system such as a standard potentiostat, galvanostat, voltmeter, or a preferably sensitive ammeter (such as a pico-ammeter) for electrode testing, determining the amount of electrons generated, and/or current collection. Preferably, the ammeter is able to measure picoamps to milliamps of current.

The invention may also include a method of testing a fluid diffusion assembly. The method includes passing the fluid through half-cell electrode assembly 16 to form a sample. The sample is contacted with indicator 18. Diffusion is an example of one type of fluid flow mechanism that may be used to contact the sample with indicator 18. A change in acidity in indicator 18 is detected. In one embodiment, detecting comprises a change in the acidity of indicator 18 due to the presence of at least one proton in indicator 18. Optionally, the step of detecting may comprise illuminating the fluorescent pH indicator with the UV lamp. Also, this method may be used to test the diffusion of the sample from assembly 16 in one or more of the three geometrical dimensions relative to assembly 16.

Figure 2:
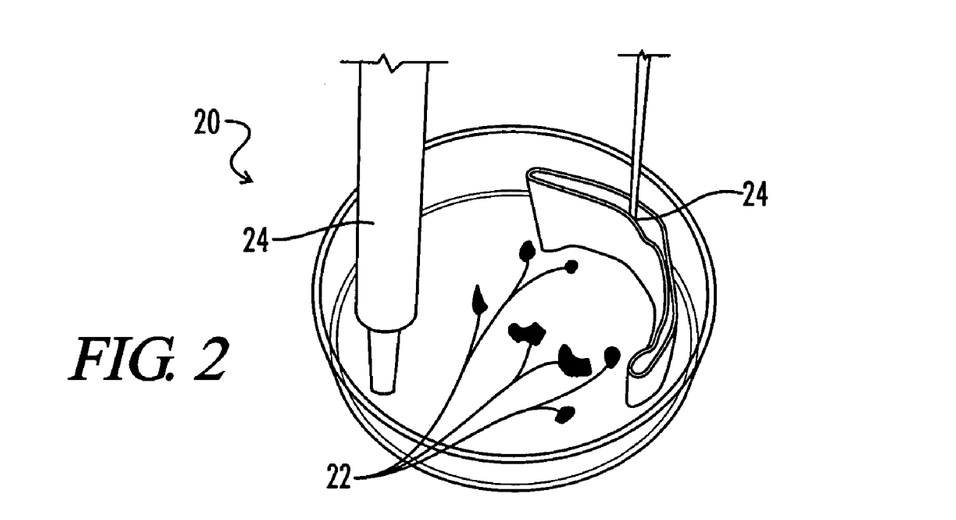
FIG. 2 is a top view of an indicator having at least one area of changed acidity.

The method may also include the step of observing at least one concentration gradient of the sample in indicator 18. This is illustrated in FIG. 2, generally designated 20. Depicted in FIG. 2 is a top view of indicator 18 having areas of change in acidity represented by circled concentration gradients 22 of protons in indicator 18. Gradient 22 may be in one or more of the three geometrical dimensions relative to assembly 16.

As depicted in FIG. 2, blue fluorescence (gradients 22) (from a quinine indicator 18 with no proton generating species or solvent) is seen in active areas along the surface of indicator 18. In FIG. 2, electrodes 24 in the solution were not applying a bias on the sample. However, FIG. 2 does demonstrate how alternate electrochemical diagnostics can be incorporated into the invention, such as, open circuit potential vs. time or cyclic voltammetry. One advantage of having electrodes 24 in indicator 18 is that the electrochemical response during operation may be measured, such as by measuring impedance or current.

The method may further include the step of altering the design of assembly 16 based on at least one of the results of the observing step. A non-exhaustive list of changes to assembly 16 includes changes to the gas diffusion layer, changes to the gas diffusion substrate, and changes to the gas delivery system (e.g., flow field plate). Examples of changes in the gas diffusion layer and gas diffusion substrate include changes in the choice of materials, pattern of openings in either the layer or the substrate, the sizes of the holes or porosity in either the layer or the substrate, and composition of either the layer or the substrate. Changes to the gas delivery system may include the design of the channels in the flow field plate, changes in the composition of the flow field plate, or changes in the thickness of the flow field plate.

The invention further includes a method for selecting a fluid permeable element for a proton exchange membrane fuel cell. The method includes the step of flowing the fluid through half-cell electrode assembly 16 to form a sample. The sample contacts indicator 18. A change in acidity in indicator 18 is detected. Preferably at least one concentration gradient 22 of the sample is observed in indicator 18. Preferably, gradient 22 is on a top surface of indicator 18. Preferably, the aforementioned steps regarding the method of selecting are conducted on a plurality of the half-cell electrode assemblies 16. The half-cell electrode assembly 16 from the plurality with the most uniform concentration of the sample, in indicator 18 is selected. In the case of multiple assemblies 16 with uniform gradients 22, the assembly 16 with the gradient 22 that has the highest color intensity is selected. Techniques to judge intensity include visualization or the below noted spectroscopy and digital image capture techniques. This method may also be used to determine a preferred fluid delivery system for a fuel cell, which multiple fluid delivery systems are proposed.

Figure 8:
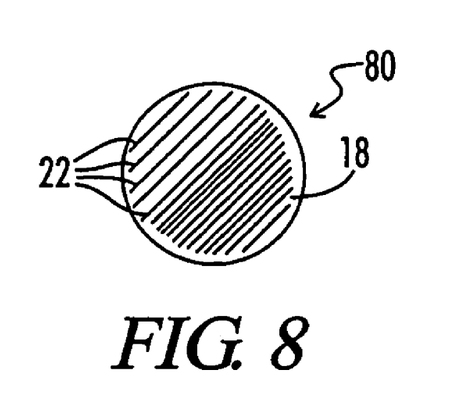
FIGS. 8 and 9 comprise two top views of indicator 18 which each include a respective concentration gradient of sample in indicator 18.
Figure 9:
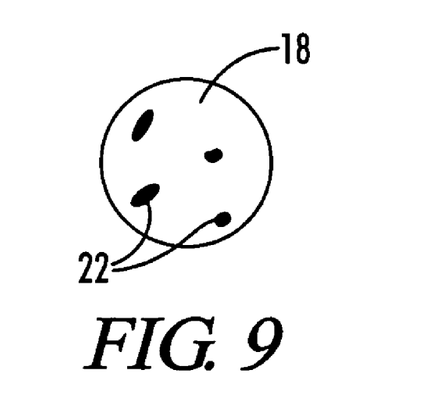

An example of what is meant by "most uniform concentration of the sample in indicator 18" is shown in FIGS. 8 and 9. FIGS. 8 and 9 are top views of indicator 18 for two different assemblies 16. The dark areas in each of FIGS. 8 and 9 represent concentration gradients 22. As depicted in FIG. 8, concentration gradients 22 has a pattern across a top surface of indicator 18 resulting from the testing of the assembly 16 for FIG. 8. In contrast, testing of assembly 16 for FIG. 9 resulted in four (4) random locations of gradients 22 on a top surface of indicator 18. Thus, the assembly, which exhibited the most uniform concentration of the sample in indicator 18 between FIGS. 8 and 9, was FIG. 8. Therefore, in selecting an assembly 16, the person of ordinary skill in the art should select the assembly associated with FIG. 8. Optionally, the method may further comprise forming the half-cell electrode assembly 16 with the most uniform concentration of the sample in indicator 18 into a fuel cell.

Furthermore, the invention includes a method of visualizing gas diffusion. The method includes the step of passing the fluid through assembly 16 to form the sample. The sample contacts indicator 18 and any change in acidity in indicator 18 is detected. Indicator 18 is observed for any concentration gradients 22 in indicator 18. The observing step may comprise viewing at least one colored area in indicator 18. Optionally, image capture, magnification, or spectroscopic tools may aid the observing step.

The method may also include the step of altering a design of half-cell electrode assembly 16 based on at least one result of the observing step. Another step that may be included into the method is the step of incorporating half-cell electrode assembly 16 into a fuel cell based on at least one result of the observing step.

This aspect of the invention may also be used to determine the flow of the fluid through the fluid permeable element of assembly 16 as compared to flow of the fluid through the catalyst. One technique of how this is accomplished is by comparing FIGS. 2 and 7.

Figure 7:
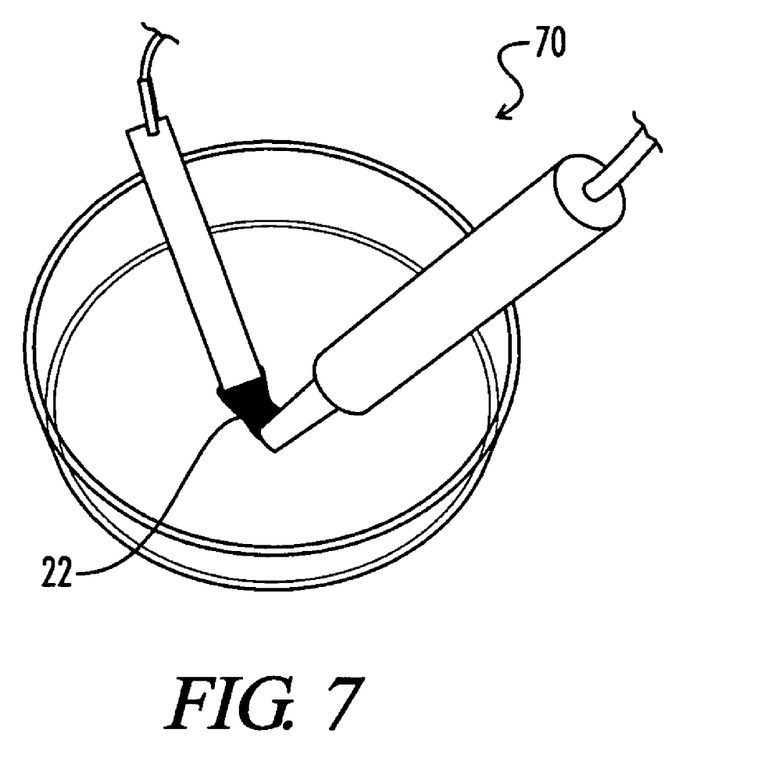
FIG. 7 is a top view of a concentration gradient 22 of sample associated with at least a portion of a catalyst in a solution of indicator 18 and an oxidizable fluid (e.g. methanol (MeOH)).

FIG. 7 is a top view of a concentration gradient 22 associated with at least a portion, preferably the entire body, of catalyst of an assembly 16 submerged in a solution of indicator 18 and a oxidizable fluid (e.g. methanol (MeOH)), generally designated 70. As depicted in FIG. 7, the presence of gradient 22 in the solution resulted in the half-cell reaction of the fluid in the solution, in the vicinity of the catalyst. This is apparent by the uniform concentration gradient 22 in the solution. This discloses to a person of ordinary skill in the art that the catalyst is uniformly coated onto the support material submerged in the solution.

A person of ordinary skill in the art could compare FIG. 7 to FIG. 2, which includes the seven (7) gradients 22. The randomness of gradients 22 in FIG. 2 would indicate to a person of ordinary skill in the art that fluid is not uniformly being flown through assembly 16 and into contact with the catalyst.

Therefore, when assembly 16 comprises a catalyst layer the method may include the steps of submerging the catalyst layer in a solution of indicator 18 and the fluid, detecting a change in acidity in the solution, and comparing a concentration gradient of change in the acidity of the solution to the concentration gradient of the sample in indicator 18. Also, the aforementioned step of submerging the catalyst in the solution may be used to analyze the uniformity of the catalyst used in assembly 16.

Another aspect of the invention includes a method of measuring gas diffusion. The steps of the method include the following: (a) passing the fluid through half-cell electrode assembly 16 to form the sample; (b) contacting the sample with indicator 18; and (c) determining a difference in the pH of a mixture of indicator 18 and the sample as compared to the pH of a solution of indicator 18 substantially free of the sample.

The method may also include the step of determining a concentration of acidic matter in the mixture. Another optional step may be determining an amount of electrons generated as a result of the passing step. Examples of suitable equipment, which may be used to determine the amount of electrons generated, include potentiostats, voltmeters, or ammeters.

The spatial resolution of active surface regions (also referred to as gradients 22) of indicator 18 demonstrates an aspect of the usefulness of this invention. The spatial resolution of gradients 22 in indicator 18 can be used to develop an understanding of how material modifications can affect gas diffusion, catalyst efficiency, proton diffusion, and the interplay between gas diffusion, catalyst efficiency and proton diffusion.

The invention may also be used to evaluate material property differences as can be seen upon comparison of material types such as, for example, carbon fiber paper versus flexible graphite sheets. The invention may be used to predict morphology differences, such as micro porosity and pore size distribution, and to evaluate differences in the diffusion of gas and subsequent delivery to the catalyst layer.

Many aspects of PEM fuel cell materials, components, and/or operational parameters can be evaluated with this invention, such as:
a) Spatial resolution of gas diffusion
   a. Effects due to operating parameters such as temperature, fuel to air stoichiometry, voltage, current, fuel, or air humidity,
b) Gas Diffusion Substrate morphology changes, and/or material changes,
c) Catalyst uniformity, deposition procedure, composition, or ink formulation,
d) Diagnostic outputs for anode or cathode half reaction:
   a. Current collection/generation,
   b. Reactant/byproduct mass transfer, and
   c. Electrode testing and efficiency—i.e., polarization curves.
e) Various indicator solutions, gels or alternate medium can be evaluated, as well as additives to the same. Alternatively these can be applied to the catalyst ink for direct detection within that layer. The same principle can be applied to the proton conduction membrane or material.
f) PEM membrane evaluations:
   a. Thickness, proton diffusion rates
   b. Membrane acidity
   c. Membrane hydration effects
   d. Membrane composition effects
   e. Membrane manufacture,
g) Flow field & MEA designs related to gas delivery to the MEA,
h) Application to alkaline cells and other industrially relevant electrochemical reactions,
i) Improved spatial resolution via Near-field Scanning Optical Microscopy and Fluorescent Imaging techniques, among other imaging or spectroscopic techniques,
j) PEM fuel cell applications—not just hydrogen but alcohol (direct methanol, etc.), acetic acid, formic acid, etc., any PEM reaction, and
k) Intrinsic material property changes during fuel cell operation such as electrical conductivity of the GDL substrate Considering the anode half-cell reaction in a hydrogen fuel cell ($H_2 \rightarrow 2H^+ + 2e^-$), it can be imagined that where active catalyst sites convert hydrogen gas into protons, there will be a localized region of higher acidity providing cage escape of the electron to preclude recombination with the protons. Preventing recombination of the electron with the proton can optionally be achieved by simply grounding the substrate in a closed circuit fashion (with or without external bias). Utilizing a common fluorescent pH indicator, a test cell for visualizing this half-cell reaction can be constructed. In a similar manner, the half-cell reaction of other proton generating fuels can be utilized for any PEM reaction. An example has been demonstrated for purposes of screening optimal catalyst compositions in methanol reactions. A converse approach can be taken to construct a test cell for the cathode half reaction, utilizing the consumption of protons as the mechanism for reaction detection, visualization, and measurement. In addition, this invention is intended to describe at least a method to evaluate the following without being limited to the below applications:

1) Gas diffusion layers consisting of various formulations, e.g., diffusion layers composed of a polymer and carbon and/or graphite
2) Proton exchange materials and/or membranes alone, and proton diffusion through the same
3) Substrates for the above—such as but not limited to gas diffusion substrates, membrane electrode assembly components (i.e., carbon fiber paper, fibrous materials, carbon or graphite-based materials, flexible graphite, etc.—with or without incorporation of the proton exchange material
4) MEA assemblies including any or all of the components for comparison such as flow-field plates, gas diffusion substrates, gas diffusion coatings, layers, membranes, catalyst support formulations, catalyst materials, and additives,
5) Flow channel designs,
6) Operational parameters such as fuel and/or oxidant gas pressure, flow rate, and composition,
7) Design and/or performance of gas diffusion substrate morphology or composition (such as fiber papers or perforated GRAFOIL® flexible graphite materials),
8) Design and/or performance of fibrous material morphology or composition (such as but not limited to carbon fiber papers), 9) Design and/or performance of conductive or non-conductive composite materials morphology or composition.

10) Anode or cathode engineering designs,

11) Electron generation or consumption can be spatially "mapped", and

12) Mass transport of water may be evaluated.

For example, use of the following technique will allow various substrates to be compared. This application of the invention has been verified with an embodiment as shown in FIG. 1 where hydrogen gas was fed into the bottom of apparatus 10. This specific example shown should not limit the general application of this invention for "mapping" the electrochemical activity. Mapping is used herein to mean at least the activity of observing gradients 22 in indicator 18 and the documentation and retention of where gradients 22 appeared in indicator 18 with respect to a particular assembly 16.

Figure 3:
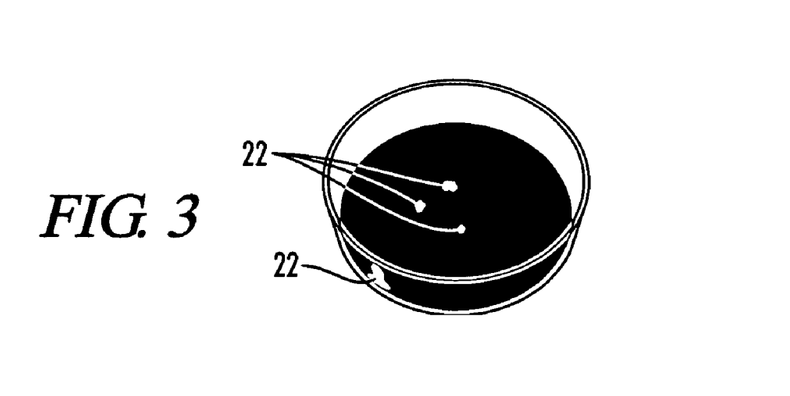
FIG. 3 shows image capture in dark conditions to directly visualize the fluorescence from the active areas of hydrogen conversion to protons.
Figure 4:
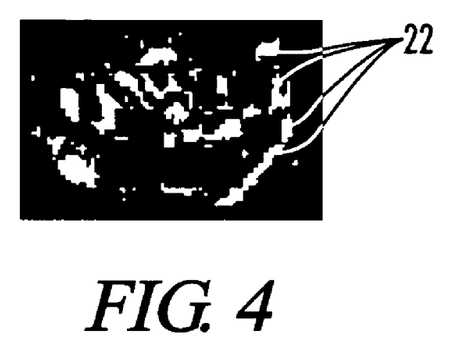
FIG. 4 is a digitally filtered image to allow improved contrast and detection of the blue fluorescence.

Digital image capture can be utilized as shown in FIGS. 3 and 4 for mapping purposes to visualize active areas of the surface of indicator 18. FIG. 3 shows image capture in dark conditions to visualize the fluorescence from the active areas (gradients 22) of hydrogen conversion to protons (or alternatively consumption of protons). In addition to mapping the location of areas 22, the intensity of areas 22 may be mapped. FIG. 4 is a digitally filtered image to allow improved contrast and detection of the blue fluorescence (gradients 22). Again, FIGS. 3 and 4 were acquired with no externally applied potential bias on the sample or indicator 18. Optional steps to enhance image resolution may include optical filtering techniques. For example, the data acquired as in FIGS. 3 and 4 above could be enhanced with the aid of CCD camera acquisition fed through narrow band pass filters, optical fluorescence microscopy, spectrometer analysis, and/or additional optical filters for hardware enhancements. These alterations may lead to better image resolution, definitive spectral analysis, and morphology correlations.

The images and visualizations such as shown in FIGS. 2, 3, and 4 will be beneficial for at least engineering a gas diffusion substrate material which is optimized and has uniform gas diffusion resulting in uniform catalyst utilization.

The delivery of gas through flow field channels, through the diffusion substrate, and reaching the catalyst can be visualized with this invention. In practice mathematical modeling can be used to predict beneficial results and to create beneficial designs for flow-field channels. The invention can be used to verify the models and/or to refine the models, thereby leading to better engineering designs. Uniformity of gas delivery to the catalyst can be visualized as above with this invention wherein discrete, localized areas (or localized increased & decreased areas) of proton generation follow the design of the flow channels.

Figure 5:
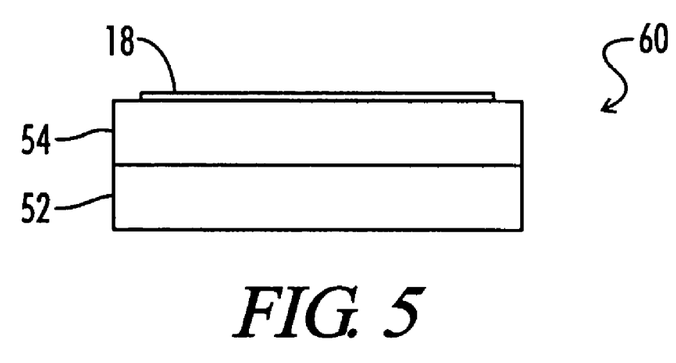
FIG. 5 is a schematic side elevation view of the alignment of a half-cell electrode assembly 16, and an indicator 18 in accordance with the invention.
Figure 6:
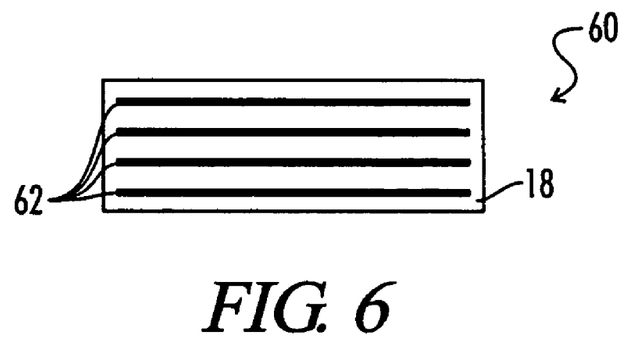
FIG. 6 is a top view of indicator 18 depicted in FIG. 5.

This application is further illustrated in FIGS. 5 and 6. FIG. 5 is a schematic side elevation view of the alignment of a half-cell electrode assembly 16, and indicator 18. Half-cell electrode assembly 16 comprises of a flow field plate 52 with channels (not shown) and a layer 54, which comprises a gas diffusion substrate, gas diffusion layer coating, and a catalyst. Preferably, indicator 18 comprises a material able to indicate the presence of protons through fluorescence.

FIG. 6 is a top view of a surface of indicator 18 shown in FIG. 5. As depicted in FIG. 6, indicator 18 includes a plurality of fluorescent areas 62. Each fluorescent area 62 represents an area of changed acidity in indicator 18 due to the presence of at least one proton. FIG. 6 indicates that the fluid is being transmitted through assembly 16 and uniformly contacting the catalyst in linear regions 64 of fluorescent areas 62. Additionally, cylindrical fuel cell designs and materials can be analyzed in a similar fashion.

The invention will be further described with the foregoing examples. The examples only include various embodiments of the invention and are not meant to limit the invention.

EXAMPLES

Example 1

Test Apparatus

A ½ MEA sample (assembly 16) was prepared with a perforated flexible graphite gas diffusion substrate (available from Graftech Inc. of Lakewood, Ohio as GRAFCELL™) with a high surface area carbon gas diffusion layer having a carbon layer (the carbon was from Cabot). A 20% Pt-carbon black catalyst was blade coated onto the gas diffusion layer. The MEA was at least about 4 thousands of an inch thick.

The MEA was placed into flange 14 of apparatus 10, schematically shown in FIG. 1. Above the MEA was indicator 18. Indicator 18 was a liquid medium composed of a dye/indicator solution with a variety of constituents that highlights subsequent dissociation of protons from the electrochemical reaction. The solution consisted of an electrolyte, fluorescent pH indicator with appropriate pKa for the reaction medium, stabilizer, and viscosity additive. Indicator 18 included about 50 ml of water, about 100 ml-molar concentration of quinine, about 1 molar concentration of an electrolyte of sodium chloride and sodium tetrafluoroborate, and up to about 90-wt % of glycerin, preferably up to about 10%. A preferred viscosity of indicator 18 was about 50 seconds when measured with a #2 Zahn cup. A UV lamp was shown onto the sample and the solution which made apparent the excitation of the fluorescent pH indicator when the pH was below the indicator pKa value for quinine.

Results And Discussion

An anode gas (hydrogen) was allowed to pass through the thickness of the MEA. Upon reaching the catalyst surface layer, hydrogen was dissociated into protons and electrons. The electrons were collected through the plane of the gas diffusion substrate and removed from the system to prevent recombination with the protons. The protons diffused through the catalyst layer and into indicator 18 residing above the top surface of the MEA. The diffusion of protons throughout the solution allowed adequate spatial resolution of the blue fluorescence from the indicator dye as shown in FIG. 2. As shown in FIG. 2, the circled areas (gradients 22) indicate regions of active hydrogen dissociation into protons from the anode.

Example 2

Example 2 is an example of verification that relatively uniform catalyst material is being deposited is stated below. In this example, the fluid was methanol and reaction was the oxidation reaction resulting in hydrogen dissociating from the methanol. The gas diffusion layer ("GDL") sample comprised of a gas diffusion substrate, GDL coatings, and catalyst layer was immersed in a methanolic solution of dye indicator 18. An anodic potential was applied to the GDL/catalyst material and protons generated from the methanol oxidation reaction were visualized via fluorescence.

Results And Discussion

The surface of the indicator showed quite uniform fluorescence. This would indicate that the layer had a uniform covering of catalyst and that the catalyst material was still active. Therefore, any non-uniform proton generation from the half-cell apparatus images (as discussed above) is not due to non-uniform catalyst deposition, or poisoned (inactive) catalyst spots on the material.

Alternate embodiments of the invention can be utilized by systematically only varying one variable at a time, such as the gas diffusion substrate type, GDL coating type, composition, or morphology. Comparisons can be made that isolate a variable and allow ex-situ testing of that variable or component aside from testing in a fuel cell test station. Furthermore, other materials and/or variables can be isolated and tested in a similar fashion.

It will be apparent to those skilled in the art that various modifications and variations can be made to the present invention without departing from the spirit and scope of the invention. Thus it is intended that the present invention cover the modifications and variations of the invention provided they come within the scope of the appended claims and their equivalents.

What is claimed is:

1. A fluid diffusion testing apparatus comprising:
    a fluid capable of undergoing oxidation or reduction;
    a half-cell electrode assembly capable to receive and chemically modify said fluid,
    wherein the half-cell assembly comurises an ion exchange membrane;
    a change in acidity indicator in communication with said assembly and the chemically modified fluid; and
    a detector for detecting a change in the change in acidity indicator, wherein said detector comprises a fluorescent pH indicator and an UV lamp aligned to illuminate said fluorescent pH indicator.

2. The fluid diffusion testing apparatus according to claim 1 wherein said assembly comprises a catalyst.

3. The fluid diffusion testing apparatus according to claim 2 wherein said apparatus further comprises a fluid permeable element in communication with said catalyst, said fluid permeable element comprises at least one of a gas diffusion layer, a gas diffusion substrate, and combinations thereof.

4. The fluid diffusion testing apparatus according to claim 3 wherein said gas diffusion substrate comprises at least one of a sheet of: flexible graphite, carbon fiber paper, cotton fiber, glass fiber, asbestos, inorganic fiber, cardboard, aluminum oxide membrane, zeolite substrate, polymer material, a composite of flexible graphite and a polymer, a composite of carbon and a polymer, a composite of carbon, flexible graphite, and a polymer, and combinations thereof.

5. The fluid diffusion testing apparatus according to claim 4 wherein said membrane is positioned between said catalyst and said indicator.

6. The fluid diffusion testing apparatus according to claim 2 wherein said assembly further comprises at least one of a flow field plate, a gas diffusion layer, a gas diffusion substrate, and combinations thereof.

7. The fluid diffusion testing apparatus according to claim 1 further comprising an electrical current measuring assembly, said electrical current measuring assembly comprising a pair of electrodes disposed in said indicator and a quantifying element connected to said electrodes.

* * * * *